(12) United States Patent
Xie et al.

(10) Patent No.: US 11,220,528 B2
(45) Date of Patent: Jan. 11, 2022

(54) COMPOSITIONS AND METHODS FOR TREATING PULMONARY HYPERTENSION

(71) Applicant: Marshall University Research Corporation, Huntington, WV (US)

(72) Inventors: Zijian Xie, Saline, MI (US); Jiayan Wang, Huntington, WV (US); Sandrine V. Pierre, Huntington, WV (US); Joseph I. Shapiro, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 16/611,067

(22) PCT Filed: May 11, 2018

(86) PCT No.: PCT/US2018/032308
§ 371 (c)(1),
(2) Date: Nov. 5, 2019

(87) PCT Pub. No.: WO2018/209227
PCT Pub. Date: Nov. 15, 2018

(65) Prior Publication Data
US 2020/0165299 A1    May 28, 2020

Related U.S. Application Data

(60) Provisional application No. 62/504,947, filed on May 11, 2017.

(51) Int. Cl.
| | | |
|---|---|---|
| *A61K 38/10* | (2006.01) | |
| *A61K 38/00* | (2006.01) | |
| *A61K 38/46* | (2006.01) | |
| *C07K 14/00* | (2006.01) | |
| *C07K 7/08* | (2006.01) | |
| *A61P 9/12* | (2006.01) | |
| *A61P 9/10* | (2006.01) | |

(52) U.S. Cl.
CPC .................. *C07K 7/08* (2013.01); *A61P 9/12* (2018.01); *C07K 14/00* (2013.01); *A61K 38/00* (2013.01)

(58) Field of Classification Search
CPC ...... A61K 38/00; A61K 38/10; A61K 38/005; A61K 38/46; A61K 9/0048; A61P 9/12; A61P 9/10; C07K 14/00; C07K 7/08
See application file for complete search history.

(56) References Cited

U.S. PATENT DOCUMENTS

| | | |
|---|---|---|
| 2010/0056446 A1 | 3/2010 | Xie et al. |
| 2016/0193168 A1 | 7/2016 | Nicolls et al. |
| 2016/0331816 A1 | 11/2016 | Daniell et al. |

OTHER PUBLICATIONS

Ye, Qiqi, "Regulation of Src by a1 Na/K-ATPase," A Dissertation, Submitted to the Graduate Faculty as partial fulfillment of the requirements for the Doctor of Philosophy Degree in Biomedical Sciences, The University of Toledo, Aug. 2021, pp. 1-114. (Year: 2012).*
Liu, J., et al., Attenuation of Na/K-ATPase Mediated Oxidant Amplification with pNaKtide Ameliorates Experimental Uremic Cardiomyopathy. Sci Rep, 2016. 6: p. 34592.
United States Patent and Trademark Office, International Search Report and Written Opinion issued in corresponding Application No. PCT/US18/32308, dated Aug. 7, 2018.
Chazova, et al., Pulmonary Artery Adventitial Changes and Venous Involvement in Primary Pulmonary Hypertension. American Journal of Pathology, 1995. 146(2): p. 389-397.
European Patent Office, Extended European Search Report issued in corresponding Application No. EP 18798581.7, dated Feb. 5, 2021.
Pullamsetti, S.S., et al. "Role of Src Tyrosine Kinases in Experimental Pulmonary Hypertension," Arteriosclerosis, Thrombosis, And Vascular Biology, vol. 32, No. 6, Jun. 1, 2012, pp. 1354-1365.
Li, Z., et al. "NaKtide, a Na/K-ATPase-derived Peptide Src Inhibitor, Antagonizes Ouabain-activated Signal Transduction in Cultured Cells," Journal Of Biological Chemistry, vol. 284, No. 31, Jun. 8, 2009, pp. 21066-21076.
Srikanthan, K., et al. "The Role of Na/K-ATPase Signaling in Oxidative Stress Related to Obesity and Cardiovascular Disease," Molecules, vol. 21, No. 9, Sep. 3, 2016, p. 1172.

* cited by examiner

*Primary Examiner* — Julie Ha
(74) *Attorney, Agent, or Firm* — Stites & Harbison, PLLC; Terry L. Wright

(57) ABSTRACT

Methods treating pulmonary hypertension, including pulmonary arterial hypertension, are provided, and include administering a polypeptide antagonist of a Na/K ATPase/Src receptor complex to a subject in need thereof. Administration of the polypeptide antagonist reduces pulmonary artery acceleration time, reduces an amount of right ventricular hypertrophy, reduces right ventricular wall thickness, reduces an amount of pulmonary vessel wall thickness, reduces an amount of plexiform lesions in a lung of the subject, reduces an amount of collagen deposition in a pulmonary blood vessel, reduces an amount of collagen deposition in a pulmonary blood vessel media or adventitia, and/or reduces an amount of right ventricular fibrosis. Methods of reducing pulmonary vessel wall thickness are also provided and include the administration of the polypeptide antagonist of a Na/K ATPase/Src receptor complex.

16 Claims, 14 Drawing Sheets
Specification includes a Sequence Listing.

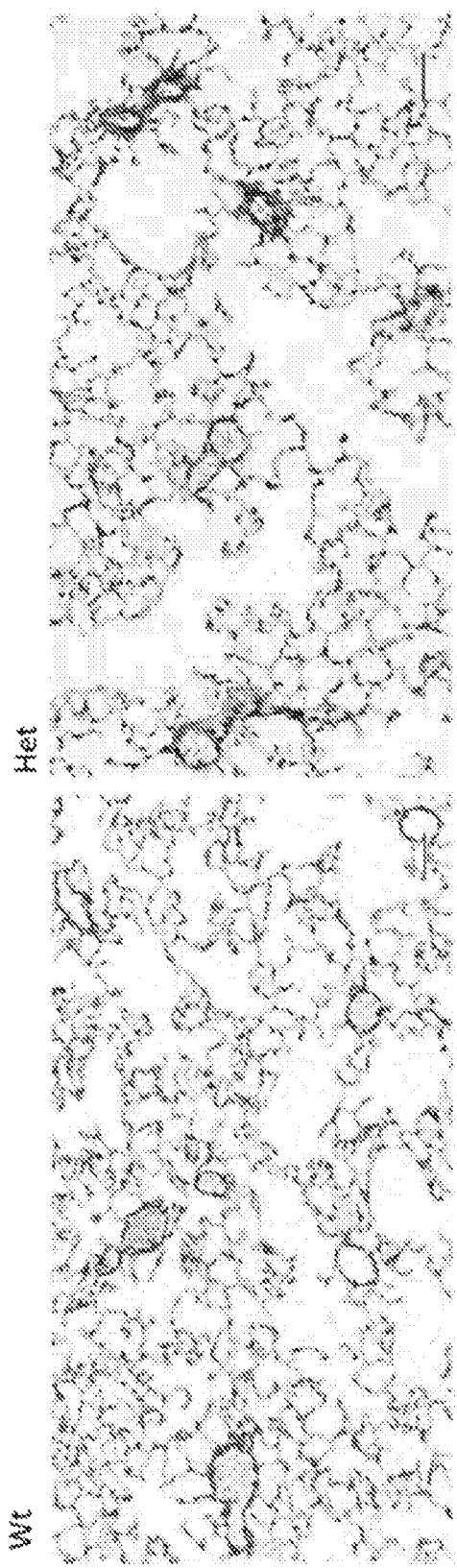
FIG. 9A
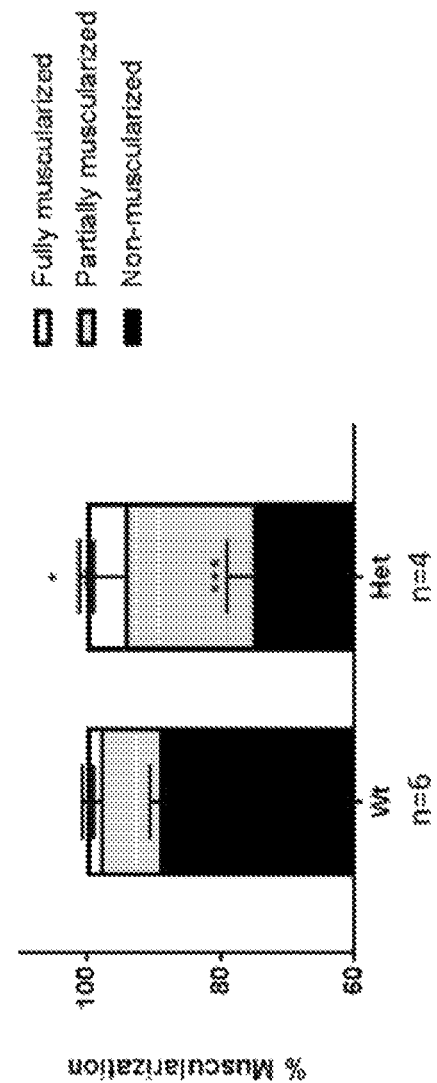
FIG. 9B

SEQUENCE LISTING

```
<160> NUMBER OF SEQ ID NOS: 9

<210> SEQ ID NO 1
<211> LENGTH: 20
<212> TYPE: PRT
<213> ORGANISM: Homo sapiens

<400> SEQUENCE: 1

Ser Ala Thr Trp Leu Ala Leu Ser Arg Ile Ala Gly Leu Cys Asn Arg
1               5                   10                  15

Ala Val Phe Gln
            20

<210> SEQ ID NO 2
<211> LENGTH: 13
<212> TYPE: PRT
<213> ORGANISM: Human immunodeficiency virus

<400> SEQUENCE: 2

Gly Arg Lys Lys Arg Arg Gln Arg Arg Pro Pro Gln
1               5                   10

<210> SEQ ID NO 3
<211> LENGTH: 16
<212> TYPE: PRT
<213> ORGANISM: Drosophila melanogaster

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 8
<212> TYPE: PRT
<213> ORGANISM: Homo sapiens

<400> SEQUENCE: 4

Lys Lys Gly Lys Lys Gly Lys Lys
1               5

<210> SEQ ID NO 5
<211> LENGTH: 33
<212> TYPE: PRT
<213> ORGANISM: Artificial Sequence
```

```
<220> FEATURE:
<223> OTHER INFORMATION: TAT NaKtide Fusion Polypeptide (pNaKtide)

<400> SEQUENCE: 5

Gly Arg Lys Lys Arg Arg Gln Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln

<210> SEQ ID NO 6
<211> LENGTH: 21
<212> TYPE: DNA
<213> ORGANISM: Artificial Sequence
<220> FEATURE:
<223> OTHER INFORMATION: IL6 Forward Primer

<400> SEQUENCE: 6
ttctctccgc aagagacttc c                                              21

<210> SEQ ID NO 7
<211> LENGTH: 21
<212> TYPE: DNA
<213> ORGANISM: Artificial Sequence
<220> FEATURE:
<223> OTHER INFORMATION: IL6 Reverse Primer

<400> SEQUENCE: 7
tgtgggtggt atcctctgtg a                                              21

<210> SEQ ID NO 8
<211> LENGTH: 20
<212> TYPE: DNA
<213> ORGANISM: Artificial Sequence
<220> FEATURE:
<223> OTHER INFORMATION: Beta Actin Forward Primer

<400> SEQUENCE: 8
agatcaagat cattgctcct                                                20

<210> SEQ ID NO 9
<211> LENGTH: 20
<212> TYPE: DNA
<213> ORGANISM: Artificial Sequence
<220> FEATURE:
<223> OTHER INFORMATION: Beta Actin Reverse Primer

<400> SEQUENCE: 9
acgcagctca gtaacagtcc                                                20
```

COMPOSITIONS AND METHODS FOR TREATING PULMONARY HYPERTENSION

RELATED APPLICATIONS

This application claims priority from U.S. Provisional Application Ser. No. 62/504,947, filed May 11, 2017, the entire disclosure of which is incorporated herein by this reference.

TECHNICAL FIELD

The presently-disclosed subject matter generally relates to compositions and methods for treating pulmonary hypertension. In particular, certain embodiments of the presently-disclosed subject matter relate to polypeptides and methods for using the polypeptides to treat pulmonary hypertension, including pulmonary arterial hypertension and associated vessel wall thickening.

BACKGROUND

The Na/K-ATPase enzyme is ubiquitously expressed in most eukaryotic cells and helps maintains the trans-membrane ion gradient by pumping $Na^+$ out and $K^+$ into cells. The Na/K-ATPase interacts directly with Src via at least two binding motifs: one being between the CD2 of the α1 subunit and Src SH2; and the other involving the third cytosolic domain (CD3) and Src kinase domain. The formation of this Na/K-ATPase and Src complex serves as a receptor for ouabain to provoke protein kinase cascades. Specifically, binding of ouabain to Na/K-ATPase will disrupt the latter interaction, and then result in assembly and activation of different pathways including ERK cascades, PLC/PKC pathway and ROS production. Moreover, this interaction keeps Src in an inactive state. Thus, the Na/K-ATPase functions as an endogenous negative Src regulator. See also International Patent Application Nos. WO 2008/054792 and WO 2010/071767, which are both incorporated herein by reference.

Src family kinases are 52-62-kDa membrane-associated nonreceptor tyrosine kinases and they participate in several tyrosine phosphorylation-related signaling pathways in response to various extracellular ligands. Src, for example, contains at least three protein interaction domains. The SH3 domain binds to polyproline motifs and the SH2 domain interacts with the phosphorylated tyrosine residues. The kinase domain reacts with the nucleotide and phosphorylates the substrate. Binding of protein ligands to the SH3 or SH2 domain can activate Src. Proteins that bind with kinase domain of Src were also reported to be capable of regulating Src activity.

It is further appreciated that the Na+/K+-ATPase interacts with Src and Src family kinases to form a functional receptor. Binding of ouabain to this receptor activates Src, which in turn phosphorylates various effectors, resulting in the assembly and activation of different pathways including the Ras/Raf/ERK1/2 and phospholipase C/protein kinase C cascades as well as increases in intracellular $Ca^{2+}$ and cellular ROS production. The activation of these signaling pathways eventually leads to changes in cardiac and renal functions, stimulation of cell proliferation and tissue fibrosis, protection of tissue against ischemia/reperfusion injury, inhibition of cancer cell growth, and more. While many known Src and Src family kinase inhibitors are developed as ATP analogs that compete for ATP binding to these kinases, such Src inhibitors lack pathway specificity. In this regard, it has previously been observed that blocking NKA/Src activation by a polypeptide designated "pNaKtide" (SEQ ID NO: 5) effectively abolishes the formation of ROS amplification loop, resulted in an inhibition of pathological ROS signaling. pNaKtide also reduced ROS stress and signaling in obesity and was effective in blocking and reversing left ventricular hypertrophy and fibrosis in an animal model of uremic cardiomyopathy.

Pulmonary arterial hypertension (PAH), defined by a resting mean pulmonary artery pressure greater than 25 mmHg, or greater than 30 mmHg with exercise, is a fatal disease in which pulmonary vascular remodeling and constriction progressively lead to cardiac right ventricular dysfunction and failure. PAH is characterized by endothelial cell proliferation, pulmonary vascular remodeling, pruning of distal vessels, and increased pulmonary resistance, culminating in right heart failure and death. The estimated prevalence of PAH ranges from 10 to 52 cases per million. Contemporary registries indicate that the 3-year and 5-year survival rates of PAH patients were 51-71% and 48-58%, respectively. The characteristic pulmonary vascular lesions in PAH include medial hypertrophy, intimal proliferative and fibrotic changes, adventitial thickening, complex lesions and thrombotic lesions. Abnormal vascular remodeling and pulmonary vasoconstriction result in elevated resistance in the pulmonary circulation and right ventricle afterload, leading to development of right ventricular hypertrophy as a compensative mechanism. Cardiac output is initially maintained, but with persistent increased resistance, progressive contractile dysfunctions occurs, leading to decompensation, dilatation, and right ventricle failure. Moreover, under the pathological conditions of PAH, the increase in ROS is key to endothelial cell and smooth muscle cells proliferation and inflammation that are the pathological basis of adverse remodeling in the lung vasculature. Survival in patients with PAH is closely related to right ventricular function, and the development of cellular hypertrophy and myocardial fibrosis are also associated with the excessive generation of ROS and lipid peroxidation.

Despite considerable advances in the management of PAH, limitations and complications of various therapies have brought the requirement for novel modalities in treating PAH. Mainly, four modalities are currently approved for PAH: calcium channel blockade, prostacyclin analogs, endothelin pathway antagonists, and nitric oxide pathway agents. Calcium channel blockers inhibit the calcium influx into vascular cells leading to relaxation of smooth muscle and vasodilatation. This can be a useful therapy, but only for 6-7% patients with PAH who have a vasodilatory response. Calcium channel blockers are contraindicated in non-responders as they may increase morbidity and mortality. Prostacyclin (PGI2), an endogenous substance produced by endothelial cells with potent vasodilation, anti-proliferative, anti-thrombotic, and anti-inflammatory activity on the pulmonary vascular bed is disrupted in PAH.

Prostacyclin synthetics and analogs have therefore been designed as therapeutic agents in PAH. In addition, the endothelin-1 (ET-1) pathway has been implicated in PAH. Specifically, ET-1 promotes vasoconstriction and proliferation by binding to its receptors ET-A (vascular smooth muscle cells) in the pulmonary vasculature. In PAH, ET-1, ET-A and ET-B (endothelial ET-1 receptor) are up regulated, and therefore endothelin receptor antagonists (ERA) have been developed as PAH therapy. In PAH, nitric oxide (NO) bioavailability in the pulmonary vasculature is decreased. NO is produced by endothelial cells and activates soluble guanylate cyclase (sGC) in the smooth muscle cells to catalyze cyclic guanosine monophosphate (cGMP), which leads to vasodilation, inhibition of platelet aggregation and smooth muscle cell proliferation. Phosphodiesterases (PDEs) are enzymes which inactivate cGMP. PDE-5 is an isozyme abundantly expressed in lungs and known to be up-regulated in PAH. PDE-5 inhibitors preserve cGMP levels and promote effects of endogenous NO, including pulmonary artery smooth muscle cell relaxation and possibly growth inhibition of vascular smooth muscle cells, making this class of medications beneficial in treating PAH.

There is no cure at the present time for pulmonary arterial hypertension, but currently approved treatment options including prostanoids, endothelin-receptor antagonists, and phosphodiesterase type-5 inhibitors have been shown to improve survival. Epoprostenol, a synthetic PGI2, was the first PAH-targeted therapy approved by the USFDA in 1995. To date, it is the only treatment that has demonstrated a reduction in mortality in PAH. Despite the clinical benefits, however, the short half-life (3-5 min), lack of stability after reconstitution necessitating ice packs for cooling, and continuous and uninterrupted IV administration of this medication made its use onerous. The most serious adverse events related to epoprostenol involve the indwelling tunneled catheter, such as site infection, sepsis, and catheter associated venous thrombosis. There is also a potential risk of fatal rebound PAH if the pump malfunctions or infusion is otherwise disrupted. Common side effects, which are similar for all of the PGI2 agents, include headache, flushing, jaw pain, and diarrhea. Other prostanoid analogs, with longer half-life/stability and formulations allowing multiple routes of administration including SC, IV, oral, and inhalation have been approved and positively impact hemodynamics, symptoms, quality of life, and/or 6-min walk distance as monotherapy or combination treatments. Likewise, a highly selective agonist of the prostacyclin receptor positively affected endpoints as an oral alternative to prostacyclin analogs for the treatment of PAH, but did not decrease mortality regardless of the background therapy.

Dual or selective ERAs have also been developed and improved since 2001. Overall, they have demonstrated sustained improvements in exercise capacity and a low risk of clinical worsening and death in patients with PAH. For some, concerns of drug interactions including all usual estroprogestative contraception, as well as commonly used medications such as cyclosporine, simvastatin, warfarin, and rifampin remain. Importantly all of the ERAs, including bosentan, have the potential for drug interactions with many antiretroviral therapies used to treat HIV and AIDS. They are also teratogenic and pregnancy is a formal contraindication.

Currently, two PDE-5i and one soluble guanylate cyclase stimulator are approved by the US FDA for the treatment of PAH. Overall, they have favorable effects on WHO functional class and time to clinical worsening. Drug-drug interaction and risks of hypotension (as well as headache, flushing, nasal congestion, dyspepsia and myalgia) due to systemic vasodilatory effects are the main risks.

Clearly, there is an unmet need in care for patients with pulmonary hypertension. Hence, there remains a need for compositions and methods for treating pulmonary hypertension.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes compositions and methods for treating pulmonary hypertension. In particular, certain embodiments of the presently-disclosed subject matter include polypeptides and methods for using the polypeptides to treat pulmonary hypertension, including pulmonary arterial hypertension and associated vessel wall thickening.

In some embodiments, a method for treating pulmonary hypertension is provided that comprises administering a polypeptide antagonist of a Na/K ATPase/Src receptor complex to a subject in need thereof. In some embodiments, the polypeptide antagonist comprises the sequence of SEQ ID NO: 1, or a functional fragment, and/or functional variant thereof. In some embodiments, the polypeptide antagonist further includes a cell penetrating polypeptide encoded by an amino acid sequence selected from the group consisting of SEQ ID NOS: 2-4. In some embodiments, such a polypeptide antagonist including a cell pepetrating peptide comprises the sequence of SEQ ID NO: 5, or a functional fragment, and/or functional variant thereof.

In some embodiments, administration of the polypeptide antagonist in accordance with the presently-disclosed subject matter reduces or treats one or more of the underlying causes and/or symptoms of pulmonary hypertension. For example, in some embodiments, administering the polypeptide antagonist reduces pulmonary artery acceleration time, reduces an amount of right ventricular hypertrophy, reduces right ventricular wall thickness, reduces an amount of pulmonary vessel wall thickness, reduces an amount of plexiform lesions in a lung of the subject, reduces an amount of collagen deposition in a pulmonary blood vessel, reduces an amount of collagen deposition in a pulmonary blood vessel media or adventitia, reduces an amount of right ventricular fibrosis, and/or reduces an amount of IL-6 in the subject.

In some embodiments, the pulmonary hypertension treated in accordance with the presently-disclosed subject matter is pulmonary arterial hypertension such that, in certain embodiments, a method for treating pulmonary arterial hypertension is provided that comprises administering a polypeptide antagonist of a Na/K ATPase/Src receptor complex to a subject in need thereof.

Further provided, in some embodiments, are methods of reducing pulmonary vessel wall thickness. In some embodiments, a method of reducing pulmonary vessel wall thickness is provided that comprised administering a polypeptide antagonist of a Na/K ATPase/Src receptor complex to a subject in need thereof. In some embodiments, such a subject has pulmonary arterial hypertension.

Further features and advantages of the presently-disclosed subject matter will become evident to those of ordinary skill in the art after a study of the description, figures, and non-limiting examples in this document.

BRIEF DESCRIPTION OF THE SEQUENCE LISTING

The following is a brief description of the Sequence Listing that is attached hereto and is hereby incorporated by reference in its entirety.

SEQ ID NO: 1 is an amino acid sequence encoding an embodiment of a polypeptide in accordance with the presently-disclosed subject matter (NaKtide, SATWLALSRIAGLCNRAVFQ);

SEQ ID NO: 2 is an amino acid sequence encoding a TAT cell penetrating peptide (GRKKRRQRRRPPQ);

SEQ ID NO: 3 is an amino acid sequence encoding a penetratin (AP) cell penetrating peptide (RQIKIWFQNRRMKWKK);

SEQ ID NO: 4 is an amino acid sequence encoding the N-terminal poly-lysine domain of the al subunit of Na/K-ATPase (AlN, KKGKKGKK);

SEQ ID NO: 5 is an amino acid sequence encoding an embodiment of another polypeptide in accordance with the presently-disclosed subject matter (pNaKtide, GRKKRRQRRRPPQSATWLALSRIAGLCNRAVFQ);

SEQ ID NO: 6 is a forward primer for analyzing IL-6 expression (TTC TCT CCG CAA GAG ACT TCC);

SEQ ID NO: 7 is a reverse primer for analyzing IL-6 expression (TGT GGG TGG TAT CCT CTG TGA);

SEQ ID NO: 8 is a forward primer for analyzing (3-actin expression (AGA TCA AGA TCA TTG CTC CT); and SEQ ID NO: 9 is a reverse primer for analyzing (3-actin expression (ACG CAG CTC AGT AAC AGT CC).

BRIEF DESCRIPTION OF THE DRAWINGS

(FIG. 1A) pulmonary artery acceleration time (PAAT); (FIG. 1B) Fulton index; (FIG. 1C) RV thickness assessed by echocardiography; (FIG. 1D) a representative trace of right ventricular systolic pressure (RVSP); and (FIG. 1E) RVSP. Values are mean±SEM. , * and **** indicate p<0.01, p<0.001 and p<0.0001 vs indicated group. n=4-14 per group.

(FIG. 3A) images showing representative PLs in H&E stained sections of HxSu and treatments with pNaKtide; and (FIG. 3B) a graphs showing the number of PLs. Values are mean±SEM, * and **indicate p<0.05 and p<0.01 vs indicated group. n=4-8 per group. Bar=100 μm.

(FIG. 5A) representative images of accumulation of collagen in right ventricle with PSR staining; and (FIG. 5B) a graph of the quantification of cardiac fibrosis. n=4 for each group. ***, p<0.001 vehicle vs control; ###, p<0.001 pNaKtide vs. vehicle. Bar=100 μm.

(FIG. 7A) images of representative Western blot of protein carbonylation in lung homogenates; and (FIG. 7B) a graph showing quantitative data of protein carbonylation in lung homogenates. Values are mean±SEM, * and ** indicate P<0.05 and P<0.01, n=3-5 per group.

(FIG. 8A) a graph showing RV/LV+S weight ratios in mCBM mice, where right and left ventricles including septum (S) were dissected free of connective tissues from age- and sex-matched 6-month-old mice and weighed; (FIG. 8B) a graph showing increased RV/body weight in mCBM heterozygous mice; (FIG. 8C) representative RVSP Tracings; and (FIG. 8D) increased RVSP in mCBM heterozygous mice, where RVSP was measured in age- and sex-matched 6-month-old mice. Data are expressed as mean±SEM. *P<0.01, **P<0.01. mCBM WT versus heterozygous (n=6-8)

FIGS. 9A-9B include graphs and images showing pulmonary artery muscularization in Het mice, where the left lung from wt and het mice were inflated with 10% formalin, processed for histologic assessment, and then stained with anti-vWF and anti α-SMA, including: (FIG. 9A) representative immunohistochemistry images of lung vessels in wt and het mice; (FIG. 9B) images and a graphs showing the extent of α-SMA staining as a measure of pulmonary artery muscularization as assessed in small vessels (30-70 μm), where the vessels were assigned as non-muscularised (no α-SMA staining), partially muscularised, or fully muscularised (thick unbroken wall of smooth muscle), and where the percentage distribution of each was calculated per group. Vessels were counted in 15 fields (magnification 20×) of each lung section per animal. Data are the mean±SEM, n=4-6 per group. * P<0.05,  P<0.01 and * P<0.001. Scale bar: 50 μm.

DESCRIPTION OF EXEMPLARY EMBODIMENTS

Figure 1A:
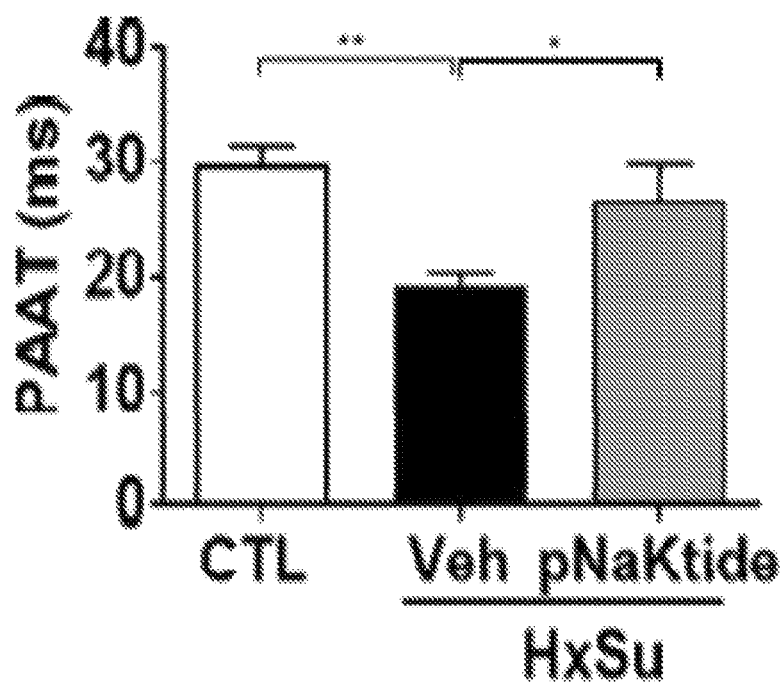
FIGS. 1A-1E include graphs showing that pNaKtide decreases pulmonary arterial hypertension (PAH) and right ventricular (RV) hypertrophy, including graphs showing.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

It will be understood that various details of the presently disclosed subject matter can be changed without departing from the scope of the subject matter disclosed herein. Furthermore, the description provided herein is for the purpose of illustration only, and not for the purpose of limitation.

Additionally, while the terms used herein are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Furthermore, following long-standing patent law convention, the terms "a", "an", and "the" refer to "one or more" when used in this application, including the claims. Thus, for example, reference to "a polypeptide" includes a plurality of such polypeptide, and so forth. Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes compositions and methods for treating pulmonary arterial hypertension. The term "pulmonary hypertension" is used herein to refer to an increased pressure in the blood vessels of the lungs of a subject, and that affects those vessel as well as the right side of a heart of a subject. Such pulmonary hypertension can be classified into a number of groups based on the causes of the pulmonary hypertension, and can include pulmonary arterial hypertension, pulmonary hypertension caused by left-sided heart disease, pulmonary hypertension caused by lung disease, pulmonary hypertension caused by blood clots, as well as pulmonary hypertension caused by other conditions.

In some embodiments, however, the pulmonary hypertension treated in accordance with the presently-disclosed subject matter is pulmonary arterial hypertension. In this regard, the term "pulmonary arterial hypertension," as used herein, is used to refer what is typically categorized as Group I pulmonary hypertension as defined by the World Symposium on Pulmonary Hypertension, and includes idiopathic and heritable PAH, as well as PAH associated with diseases of the connective tissue (scleroderma, lupus, and the like), PAH induced by drugs or toxins, HIV infection, portal hypertension, congenital heart disease, and schistosomiasis.

In some embodiments of the presently-disclosed subject matter, methods and compositions are provided that make use of or include a polypeptide useful for treating pulmonary hypertension. In some embodiments, the polypeptide is a polypeptide that reduces or inhibits the receptor function of the Na/K-ATPase and Src complex. In some embodiments, the polypeptide is an antagonist for the receptor function of the Na/K-ATPase and Src complex. The terms "polypeptide," "protein," and "peptide" are used interchangeably herein to refer to a polymer of the protein amino acids regardless of its size or function. The terms "protein," "polypeptide," and "peptide" are used interchangeably herein to also refer to a gene product, homologs, orthologs, paralogs, fragments, any protease derived peptide (fragment), and other equivalents, variants, and analogs of a polymer of amino acids.

In some embodiments, the polypeptides are comprised of the sequence of SEQ ID NO: 1 (NaKtide), or fragments, and/or variants thereof. The terms "polypeptide fragment" or "fragment" when used in reference to such a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus of the reference polypeptide, the carboxy-terminus of the reference polypeptide, or both. Polypeptide fragments can also be inclusive of "functional fragments," in which case the fragment retains some or all of the activity of the reference polypeptide.

The term "variant," as used herein, refers to an amino acid sequence that is different from the reference polypeptide by one or more amino acids. In some embodiments, a variant polypeptide may differ from a reference polypeptide by one or more amino acid substitutions. For example, a NaKtide polypeptide variant can differ from the NaKtide polypeptide of SEQ ID NO: 1 by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiments, the present polypeptides include polypeptides that share at least 75% homology with the NaKtide polypeptide of SEQ ID NO: 1. In some embodiments, the polypeptides share at least 85% homology with the NaKtide polypeptide of SEQ ID NO: 1. In some embodiments, the polypeptides share at least 90% homology with the NaKtide polypeptide of SEQ ID NO: 1. In some embodiments, the polypeptides share at least 95% homology with the NaKtide polypeptide of SEQ ID NO: 1.

"Percent identity," or "percent homology" when used herein to describe to an amino acid sequence or a nucleic acid sequence, relative to a reference sequence, can be determined using the formula described by Karlin and Altschul. Such a formula is incorporated into the basic local alignment search tool (BLAST) programs of Altschul et al.

Embodiments of the present polypeptides can further comprise one or more leader sequences, and in some embodiments, the leader sequences include, but are not limited to, cell penetrating peptides (CPPs). The term "cell penetrating peptide" (CPP) is used herein to generally refer to short peptides that can or that assist in facilitating the transport of molecular cargo across plasma membranes found in a cell. In some instances, the molecular cargo includes another polypeptide, such as the polypeptides described herein. Of course, the cell penetrating peptides can be conjugated to the molecular cargo (e.g., polypeptide) via any number of means, including covalent bonds and/or non-covalent bonds. In a number of instances, however, such cell penetrating peptides will often include a relatively high concentration of positively-charged amino acids, such as lysine and arginine, and will have a sequence that contains an alternating pattern of charged (polar) and non-charged amino acids.

In some embodiments of the presently-disclosed subject matter, an exemplary leader sequence or cell-penetrating peptide can include the trans-activating transcriptional activator (TAT) cell penetrating peptide, which is represented by the sequence of SEQ ID NO: 2. Addition of TAT sequence to NaKtide generates pNaKtide. Another exemplary leader sequence includes penetratin (AP), which is represented by the sequence of SEQ ID NO: 3. Yet another exemplary leader sequence includes an amino acid sequence encoding the N-terminal poly-lysine domain of the al subunit of Na/K-ATPase (AlN), which is represented by the sequence of SEQ ID NO: 4. Those of ordinary skill will appreciate though that other leader sequences, including other cell penetrating peptides, can also be used in conjunction with the presently-disclosed polypeptides. In some embodiments, a polypeptide including a leader sequence, such as a cell penetrating peptide, attached to the NaKtide sequence of SEQ ID NO: 1 is referred to herein as a pNaKtide (e.g., SEQ ID NO: 5; GRKKRRQRRRPPQSATWLALSRIAGLCN-RAVFQ, which includes the TAT cell penetrating peptide of SEQ ID NO: 2 fused to the NaKtide sequence of SEQ ID NO: 1).

The presently-disclosed subject matter further includes and makes use of pharmaceutical compositions comprising the polypeptides described herein as well as a pharmaceutically-acceptable carrier. Indeed, when referring to certain embodiments herein, the terms "polypeptide" and/or "composition" can be used interchangeably herein to refer to a pharmaceutical composition that includes the polypeptide.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of polypeptide to biodegradable polymer and the nature of the particular biodegradable polymer employed, the rate of polypeptide release can be controlled. Depot injectable formulations can also be prepared by entrapping the polypeptide in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the polypeptides can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

As indicated herein, the presently-disclosed subject matter further includes methods for treating pulmonary hypertension, including pulmonary arterial hypertension, with a polypeptide of the presently-disclosed subject matter (e.g., a polypeptide of SEQ ID NO:5). In some embodiments, a method of treating pulmonary hypertension is provided that comprises administering one of the presently-disclosed polypeptides to a subject in need thereof. In some embodiments, administration of such a polypeptide treats pulmonary hypertension by inhibiting or reducing the receptor function of the Na/K-ATPase and Src complex. In some embodiments, the polypeptides inhibit or reduce the receptor function by acting as an antagonist of the Na/K-ATPase and Src complex.

The terms "reducing," "reduction," "inhibiting," "inhibition" and grammatical variations thereof do not necessarily refer to the ability to completely inactivate all target biological activity in all cases. Rather, the skilled artisan will understand that those terms refer to decreasing biological activity of a target, such as can occur when a ligand binds a site of the target, a protein in a biochemical pathway of the target is blocked, a non-native complexes with a target, or the like. Such decrease in biological activity can be determined relative to a control, wherein the control can be representative of an environment in which an inhibitor is not administered. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. In some embodiments, the increases and/or decreases described herein can be in reference to a control subject having pulmonary hypertension and that has not been treated with one of the presently-disclosed polypeptides. In other embodiments, the increases and/or decreases described herein can be in reference to a baseline obtained in a subject that is in need of treatment, but has not yet began a particular therapeutic regimen.

The terms "treatment" or "treating," as used herein, refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another therapy directed toward the improvement of the associated disease, pathological condition, or disorder.

The treatment of a pulmonary hypertension can be measured and quantified in several different ways. For example, in some embodiments, treatment of pulmonary arterial hypertension can be measured and quantified by, among other things, precapillary pulmonary hypertension (an elevated mean pulmonary arterial pressure ≥25 mmHg, a normal pulmonary artery wedge pressure of ≤15 mmHg) and pulmonary vascular resistance (PVR) >3 Wood units, remodelling of the right ventricle, right-sided heart failure, right ventricular systolic pressure, vascular endothelial dysfunction, pulmonary arterial wall hypertrophy, or a combination thereof. Alternatively or additionally, treatment of pulmonary arterial hypertension can be evaluated by the six minute walking distance, time to worsening, occurrence of death, need for lung transplantation, need for atrial septostomy. Treatment of pulmonary arterial hypertension can also be characterized by a decrease in endothelial cell proliferation, pulmonary vascular remodeling, pruning of distal vessels, and pulmonary resistance. measurement of the subject prior to treatment with one of the presently-discloses polypeptides.

In some embodiments, administration of the polypeptide antagonist in accordance with the presently-disclosed subject matter reduces or treats one or more of the underlying causes and/or symptoms of pulmonary hypertension. For example, in some embodiments, administering the polypeptide antagonist reduces pulmonary artery acceleration time, reduces an amount of right ventricular hypertrophy, reduces right ventricular wall thickness, reduces an amount of pulmonary vessel wall thickness, reduces an amount of plexiform lesions in a lung of the subject, reduces an amount of collagen deposition in a pulmonary blood vessel, reduces an amount of collagen deposition in a pulmonary blood vessel media or adventitia, reduces an amount of right ventricular fibrosis, and/or reduces an amount of IL-6 in the subject. In some embodiments, a method of reducing pulmonary vessel wall thickness is provided that comprises administering a polypeptide antagonist of the presently-disclosed subject matter. Measurement of such foregoing reductions can be performed using routine procedures known to those of ordinary skill in the art.

For administration of a therapeutic composition as disclosed herein (e.g., a polypeptide of SEQ ID NO: 5), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments, the administration of the composition is via oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

Regardless of the route of administration, the compositions of the presently-disclosed subject matter are typically administered in amount effective to achieve the desired response. As such, the term "effective amount" is used herein to refer to an amount of the therapeutic composition (e.g., a polypeptide of SEQ ID NO: 5 and a pharmaceutically vehicle, carrier, or excipient) sufficient to produce a measurable biological response (e.g., a decrease in pulmonary hypertension). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

The present methods can be performed on a wide variety of subjects. Indeed, the term "subject" as used herein is not particularly limited. The term "subject" is inclusive of vertebrates, such as mammals, and the term "subject" can include human and veterinary subjects. Thus, the subject of the herein disclosed methods can be a human, non-human primate, horse, pig, rabbit, dog, sheep, goat, cow, cat, guinea pig, rodent, or the like. The term does not denote a particular age or sex. Thus, adult and newborn subjects, as well as fetuses, whether male or female, are intended to be covered.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. The examples may include compilations of data that are representative of data gathered at various times during the course of development and experimentation related to the presently-disclosed subject matter.

EXAMPLES

Materials and Methods

Rat model of Sugen5416/Hypoxia (HxSu)-induced PAH and pNaktide treatment. Adult male Sprague-Dawley rats, aged 8 weeks, weighing 300-330 g, were injected subcutaneously with Sugen 5416 weekly, and housed in a hypoxic chamber for up to 4 weeks, as described previously. Animals received pNaKtide or vehicle (normal saline) treatment via intraperitoneal injection at a dose of 1, 10 and 25 mg/kg weekly.

Echocardiographic Assessment. At 4 weeks, transthoracic echocardiography was performed by ultrasound on 2% isoflourane-anesthetized rats. Right ventricular wall thickness, pulmonary artery acceleration time (PAAT), cardiac output (CO) and HR were obtained as described.

Right ventricular systolic pressure measurements. After echocardiography, the animals were anesthetized with Ketamine/Xylazine cocktail. The right external jugular vein was exposed and isolated from the surrounding connective tissue. A micromanometer catheter (Millar pressure catheter, 1.0 F) was inserted in to the vein and pushed forward into the right ventricle. The pressure trace was monitored in the software to verify the catheter location and identify the RV pressure. The pressure measurements were recorded for 2 mins. Pressure data was analyzed with LabChart Pro. 8.0.

Right ventricular hypertrophy measurements. After echocardiography, the rats were euthanized and their hearts were isolated, flushed with saline, and dissected to separate the right ventricle (RV) from the left ventricle (LV) plus the septum (S). The Fulton index, which is ratio of the RV weight to LV+S weight (RV/LV+S) was determined to provide a measure for the RV hypertrophy.

Histology and Immunohistochemistry analysis. The lungs were harvested and processed as described. Briefly, the lungs were inflated with 10% formalin at 20 cm $H_2O$ pressure and fixed in 10% formalin overnight. The left lobe was blocked and embedded in paraffin. All sections were cut at 5 µm. Representative hematoxylin and eosin-stained (H&E) lung section through the hilum was coded and blindly evaluated for remodeling of pulmonary arteries in the range of 10-150 µm. The vessel wall thickness of each arteriole was measured using Image J and expressed as: 1) percentage of the vessel diameter by the formula (Ed-Id)/Ed×100, where Ed is external diameter and Id is internal diameter; 2) percentage of the vessel area by the formula $(area_{ext}-area_{int})/area_{ext}$, where $area_{ext}$ and $area_{int}$ are the areas within the external and internal boundaries of the medial wall, respectively. Between 10 and 20 measurements were made per animal, and the average was calculated. In order to show the muscularization of small pulmonary vessels, Immunohistochemical (IHC) staining was performed by double immunostaining the sections with an anti α-smooth muscle actin (SMA) antibody and anti-mouse von Willebrand factor (vWF) antibody as described previously. Plexiform lesions in HxSu rats were defined as a lesion projected outside the vessel (aneurysm-like) and that forming within the vessel lumen. The number of plexiform lesions (PLs) was counted in 20 random images at 20× magnification in the H&E stained lung section through the hilum per animal.

Picrosirius red stain and quantification. Picrosirius red (PSR) stain was performed in 5 μm paraffin sections as described previously. The sections were then serially imaged using an analyzer and polarizer oriented parallel and orthogonal to each other. Microscope conditions (lamp brightness, condenser opening, objective, zoom, exposure time, and gain parameters) were maintained throughout the imaging of all samples. A minimal threshold was set on appropriate control sections for each experiment in which only the light passing through the orthogonally oriented polarizers representing fibrous structures (i.e., excluding residual light from the black background) was included. The threshold was maintained for all images across all conditions within each experiment. The area of the transferred regions that was covered by the thresholded light was calculated and at least 10 sections/vessel per condition were averaged together (NIH ImageJ software).

Quantitative RT-PCR Analysis. Total RNA was purified from crushed whole lung using the Qiagen RNeasy mini kit according to the manufacturer's instructions (Qiagen, Crawley, UK). Five hundred nanograms of total RNA was transcribed to cDNA using QuantiTect Reverse Transcription (Qiagen). Quantitative real-time RT-PCR was performed with the Sequence Detection System ABI Prism 7700 (Applied Biosystems, Warrington, UK) using TaqMan Universal PCR Master Mix, No AmpErase UNG (Part No. 4324018) and the following gene expression assays: IL-6 (Forward: 5'-TTC TCT CCG CAA GAG ACT TCC-3' (SEQ ID NO: 6); Reverse: 5'-TGF GGG TGG TAT CCT CTG TGA-3' (SEQ ID NO: 7)) and β-actin (Forward: 5'-AGA TCA AGA TCA TTG CTC CT-3' (SEQ ID NO: 8); Reverse: 5'-ACG CAG CTC AGT AAC AGT CC-3' (SEQ ID NO: 9)). Samples were run in triplicate. Levels of gene expression in each sample were determined with the comparative Ct method.

Assessment of protein carbonylation. Lung tissue homogenates were prepared with RIPA buffer. Equal amounts of total protein (15 μg) from each sample were denatured with 6% SDS (final concentration), derivatized with 1×DNPH (freshly diluted with distilled water from 10×DNPH stock solution, 100 mM in 100% trifluoroacetic acid) to form DNP hydrazone derivatives, and then neutralized with neutralization buffer (30% of Glycerol in 2M Tris). This was followed by Western Blotting for protein carbonylation assay. Membrane Ponceau S staining was used for loading control of the protein carbonylation. To quantify the carbonylation level, optical signal densities of the protein bands from each lane were quantified. The signal density values of control samples were normalized to 1.0 with Ponceau S staining as loading control.

Generation of mice expressing the mutant caveolin binding motif of α1 Na/K-ATPase. A previously developed strategy was used to generate a knock-in mouse line expressing the CBM mutant al described above. Specifically, the F97A and F100A substitutions were introduced by 4-bp mutations in exon 4 of the α1 isoform gene. In addition, Pyu II and Nhe I restriction enzyme sites were introduced as two silent mutations for easy identification of the targeted allele. The CBM mutant mouse was generated using the Cre/LoxP gene targeting strategy.

All data were plotted using GraphPad Prism Software, Inc. (La Jolla, Calif., USA), and was represented as the mean±standard error of the mean (SEM). Results from the control and treated samples were compared using an analysis of variance followed by a Neumann-Keuls multiple comparison test. All analyses were completed using a 95% confidence interval. Data was considered significant when $p<0.05$.

Example 1—pNaKtide Decreases PAH and RV Hypertrophy in HxSu Rats

To assess the development of PAH in the HxSu rat model, PAAT, which is inversely correlated with the mean PAP and pulmonary vascular resistance was determined by transthoracic echocardiography 2% isoflourane-anesthetized rats. In the HxSu group, PAAT worsened significantly compared to the normoxic group. Treatment with pNaKtide (25 mg/kg/week) showed significantly reverse in PAAT (FIG. 1A).

Figure 1B:
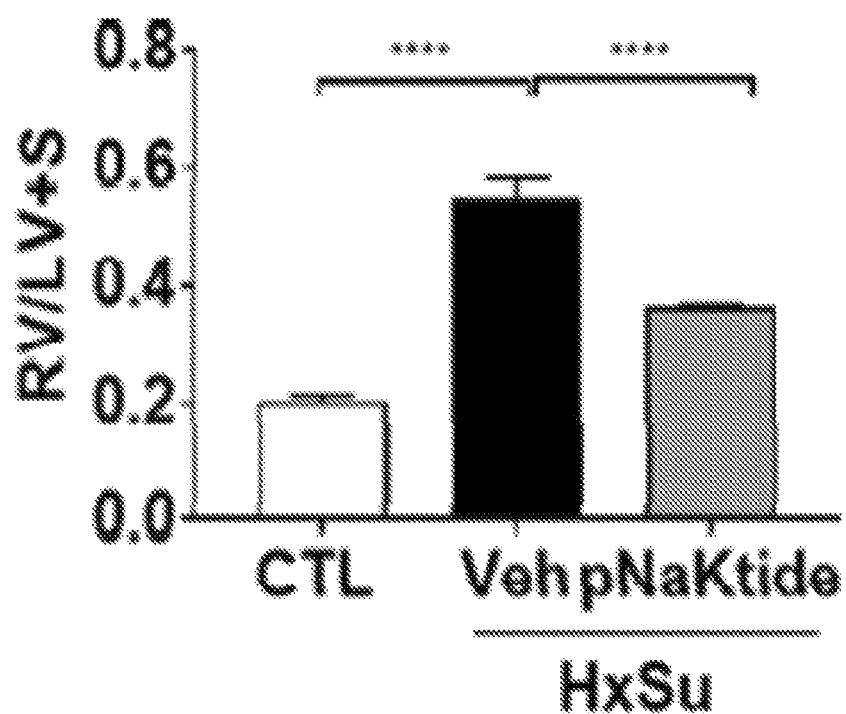
Figure 1C:
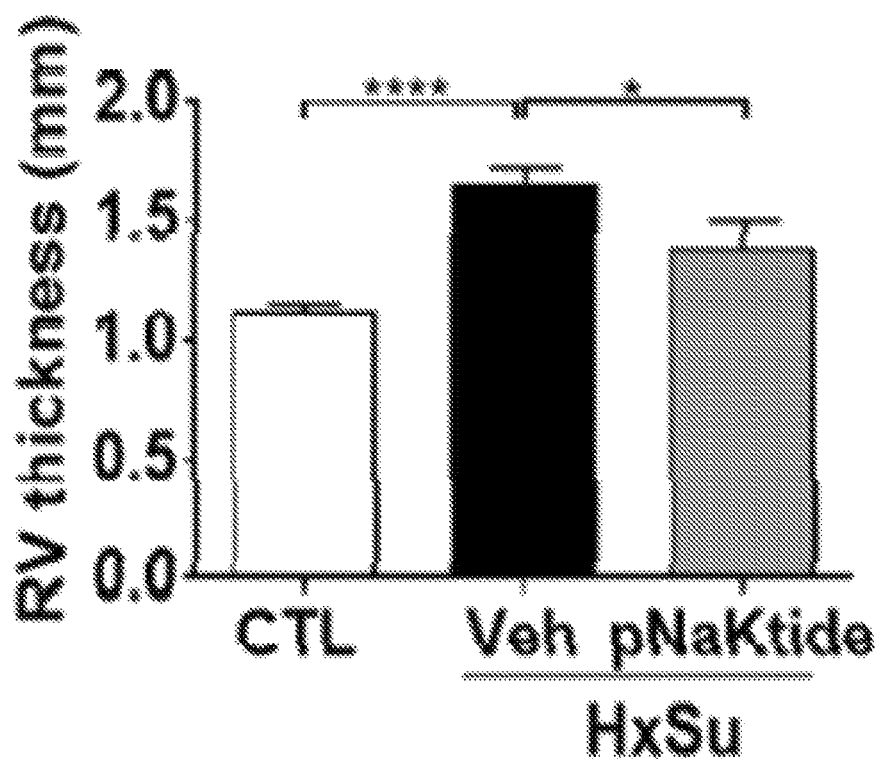

The progression of RV hypertrophy was measured by the Fulton index and echocardiography. The Fulton index (RV/LV+S) increased significantly in HxSu rats (0.55±0.04) compared with normoxic rats (0.20±0.01) and reduced on treatment with pNaKtide (0.36±0.004) (FIG. 1B). Similarly, the RV thickness assessed by echocardiography increased significantly in HxSu rats (1.65±0.07 mm) compared with normoxic rats (1.12±0.03 mm) and decreased on treatment with pNaKtide (1.37±0.11 mm) (FIG. 1C).

Figure 1D:
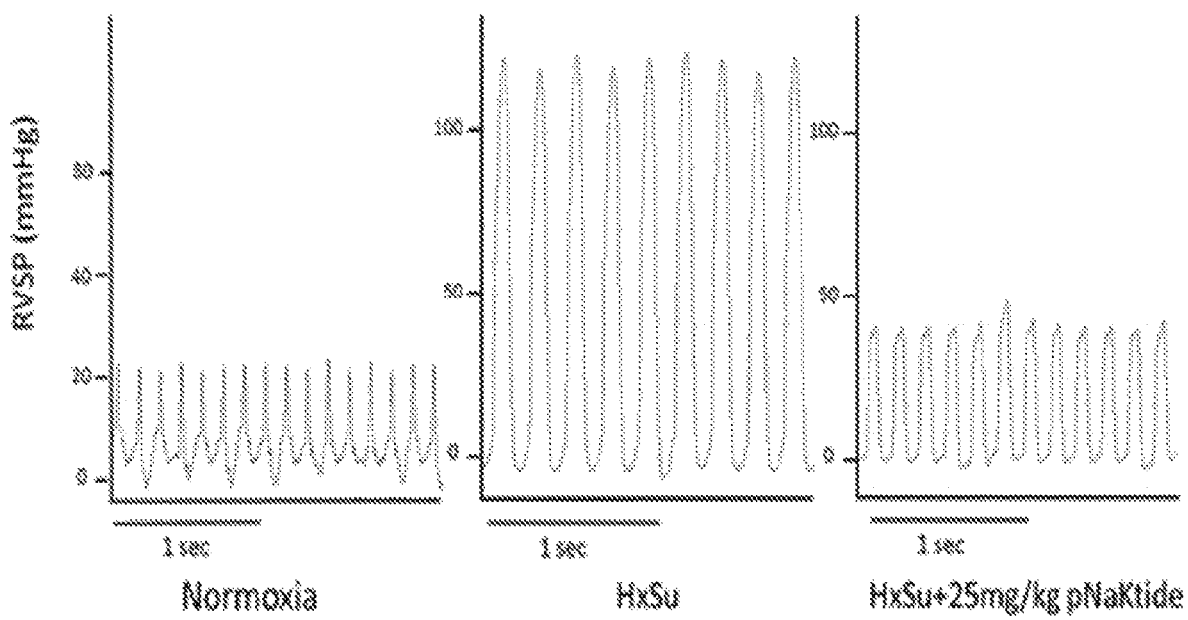
Figure 1E:
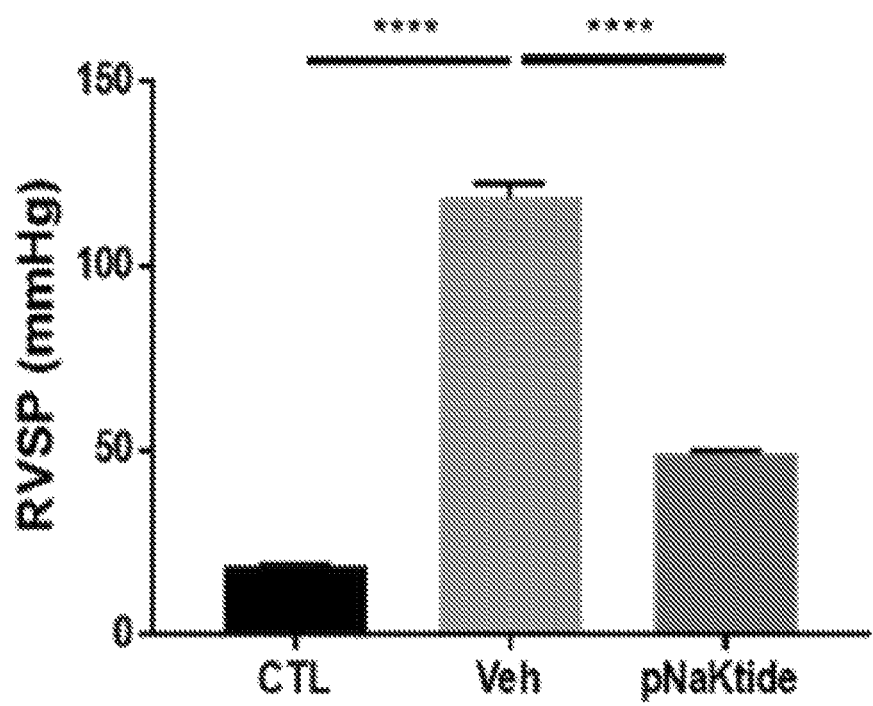

Rats exposed to HxSu also developed significantly higher right ventricular systolic pressure (RVSP) compare to normoxia group (122.6±3.9 vs. 18.7±0.3 mmHg). Treatment with pNaKtide (25 mg/kg/week) significantly decreased RVSP (49.7±0.5 mmHg) (FIGS. 1D-1E).

Figure 2:
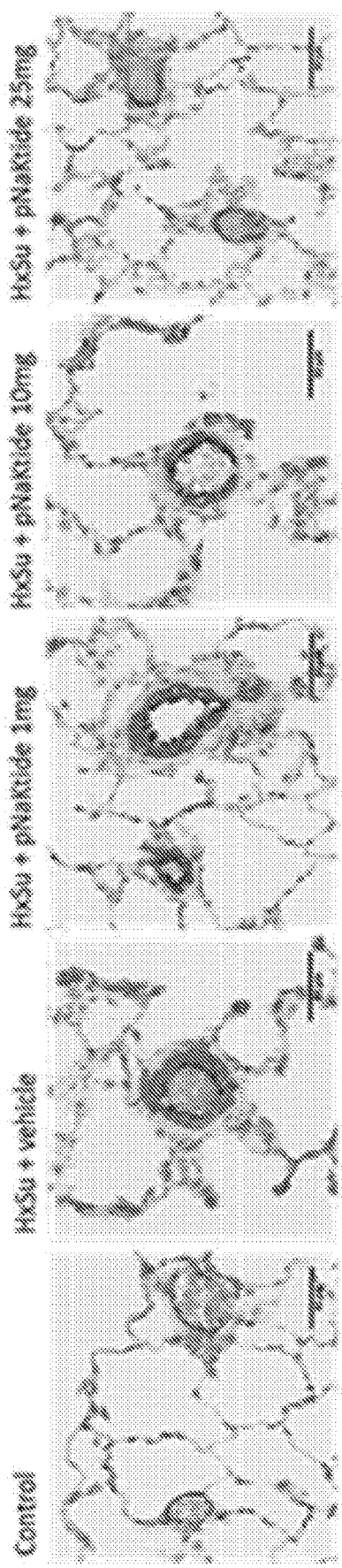
FIG. 2 includes images showing that pNaKtide decreases pulmonary vascular remodeling in PAH in a dose dependent manner in experiments where the lungs were isolated, pressure perfused, fixed, and cut at 5-μm sections, and where the images show representative smooth muscle actin (SMA) and von Willebrand Factor (vWF) stained pulmonary arterioles from normoxia, HxSu and treatments with different dose of pNaKtide groups.

Example 2—pNaKtide Decreases Pulmonary Vascular Remodeling in PAH in a Dose Dependent Manner HxSu rats developed severe vessel wall thickening compared to control rats. Representative images of the pulmonary terminal arterioles are shown in FIG. 2. Intraperitoneal injection of pNaKtide dose-dependently reduced the medial wall thickening at 1-25 mg/kg.

Example 3—Effects of pNaKtide Treatment on Plexiform Lesions (PLs)

Figure 3A:
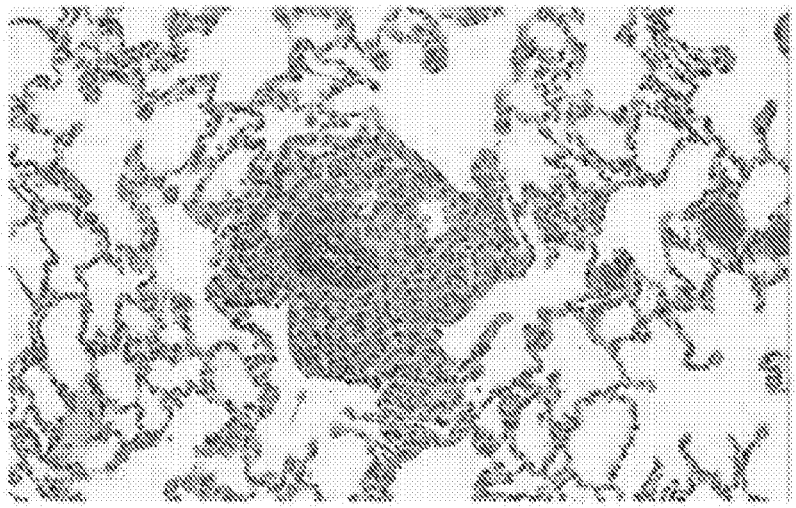
FIGS. 3A-3B are images and a graph showing pNaKtide reduces plexiform lesions (PLs) at a low dose, including.
Figure 3A:
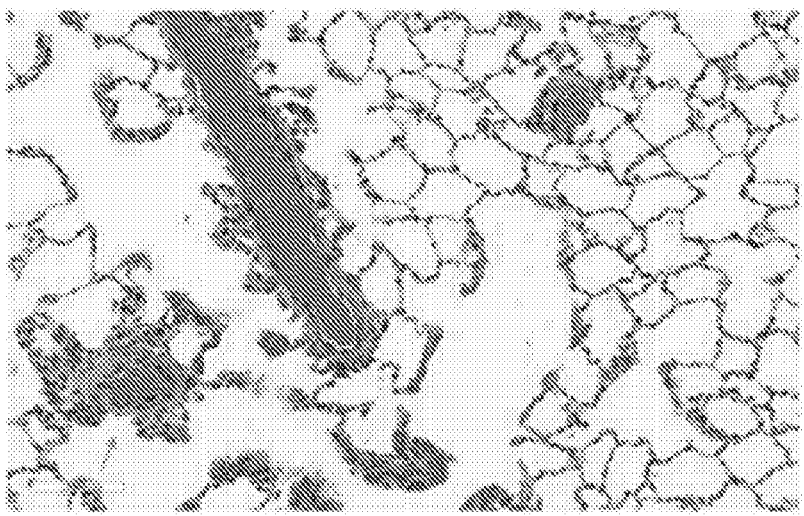
Figure 3B:
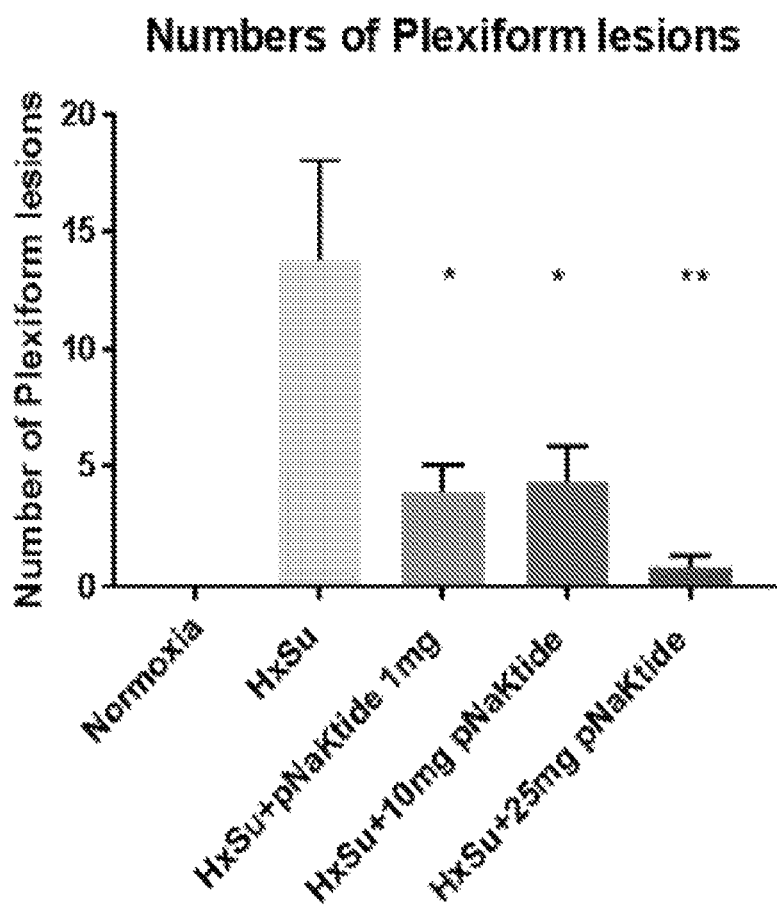

A total of 20 random fields of the H&E stained lung section through the hilum were observed at 20× magnification in each animal. No PL was found in normoxic rats. The number of PLs in HxSu rats was 13.80±4.23. The treatment of pNaKtide significantly reduced the number of PLs, even at the lowest dose (2.16±1.081 mg/kg/week)(FIG. 3B). The representative PLs are shown in FIG. 3A.

Example 4—Effects of pNaKtide Treatment on Collagen Deposition

Figure 4:
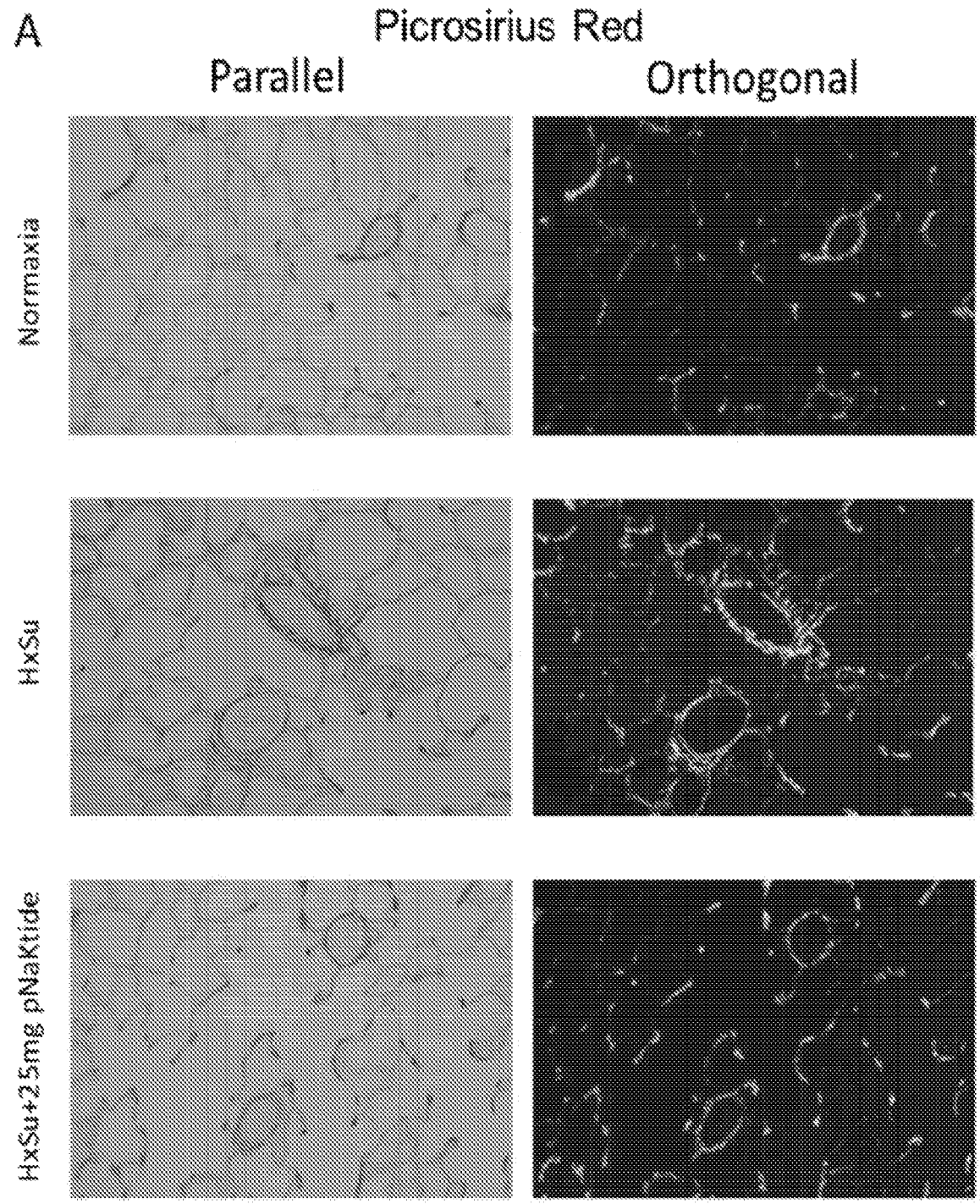
FIG. 4 includes images showing pNaKtide reduces collagen deposion in HxSu rats, where representative picrosirius red (PSR) staining images of normoxia, HxSu and treatments with pNaKtide groups are shown.
Figure 5A:
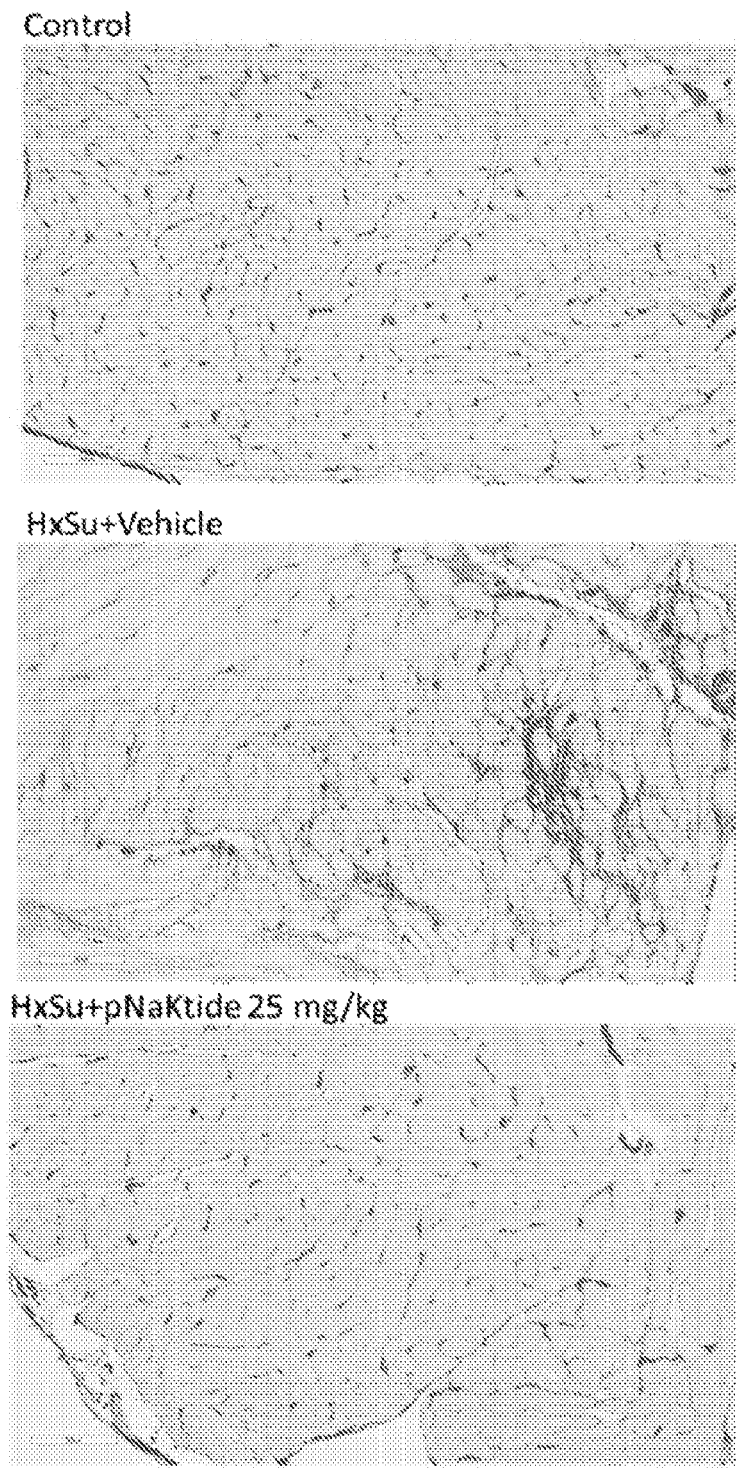
FIGS. 5A-5B includes images and a graphs showing that pNaKtide reduced collagen deposition in HxSu rats, including.
Figure 5B:
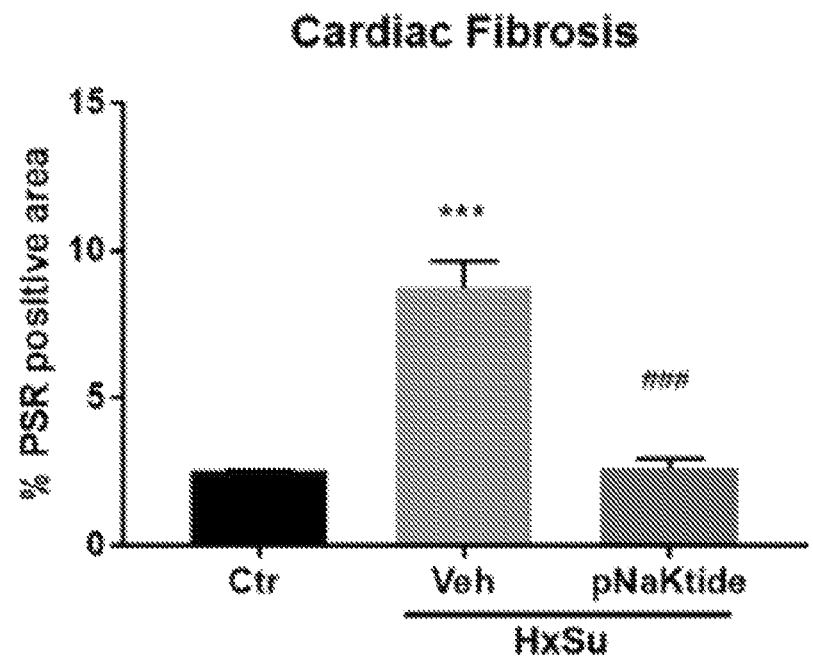

Picrosirius red staining showed an increase in collagen deposition in the vessel media and adventitia as well as lung parenchyma from HxSu group as compared with normoxia groups. Treatment with pNaKtide (25 mg/kg/week) attenuated the collagen deposition compared with HxSu group (FIG. 4). Chronic hypoxia and Su5416 caused severe RV fibrosis indicated by the accumulation of collagen. Treatment with pNaKtide normalized the fibrosis (FIGS. 5A-5B).

Example 5—pNaKtide Decreased IL-6 mRNA Level in HxSu Rat Model

Figure 6:
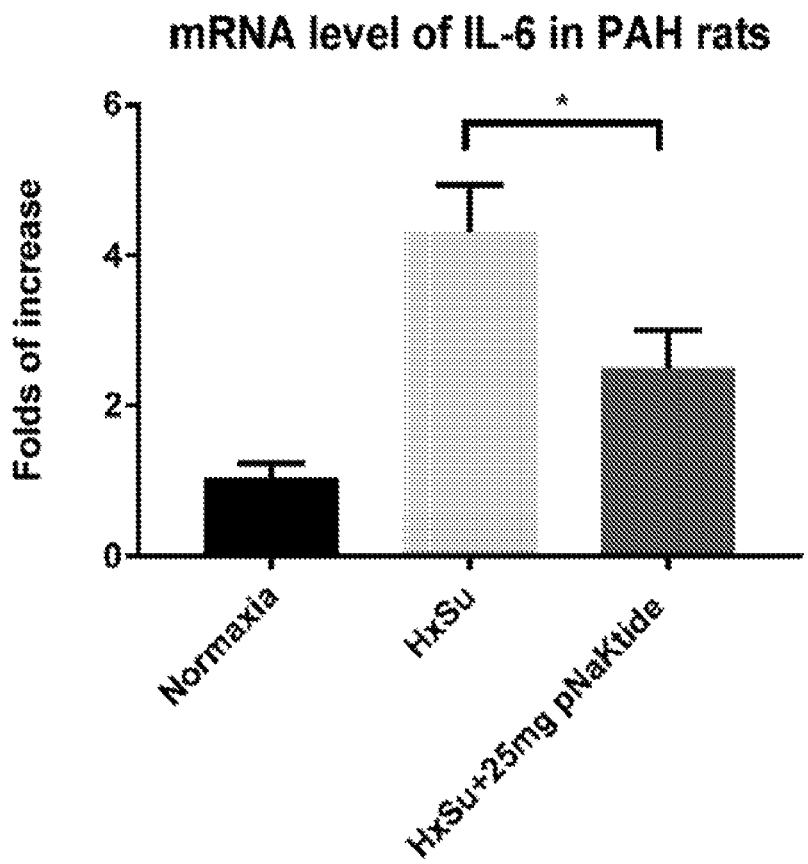
FIG. 6 is a graphs showing that pNaKtide decreased IL-6 mRNA levels in a HxSu rat model, where quantitative changes in gene expression were analyzed by quantitative real-time polymerase chain reaction (ΔΔCt method), and where mean expression in controls (normoxia) was assigned a fold change of 1, to which relevant samples were compared. Values are mean±SEM, * indicates P<0.05, n=4-6 per group.

It was further found that IL-6 mRNA levels in the lungs were considerably higher in HxSu group than in normoxic group. HxSu led to a 4-fold increase in IL-6 mRNA levels in the lungs. Treatment with pNaKtide (25 mg/kg/week) decreased the IL-6 mRNA levels by 40% compared with HxSu group (FIG. 6).

Example 6—pNaKtide Attenuated HxSu Induced Protein Carbonylation in the Lung

Figure 7A:
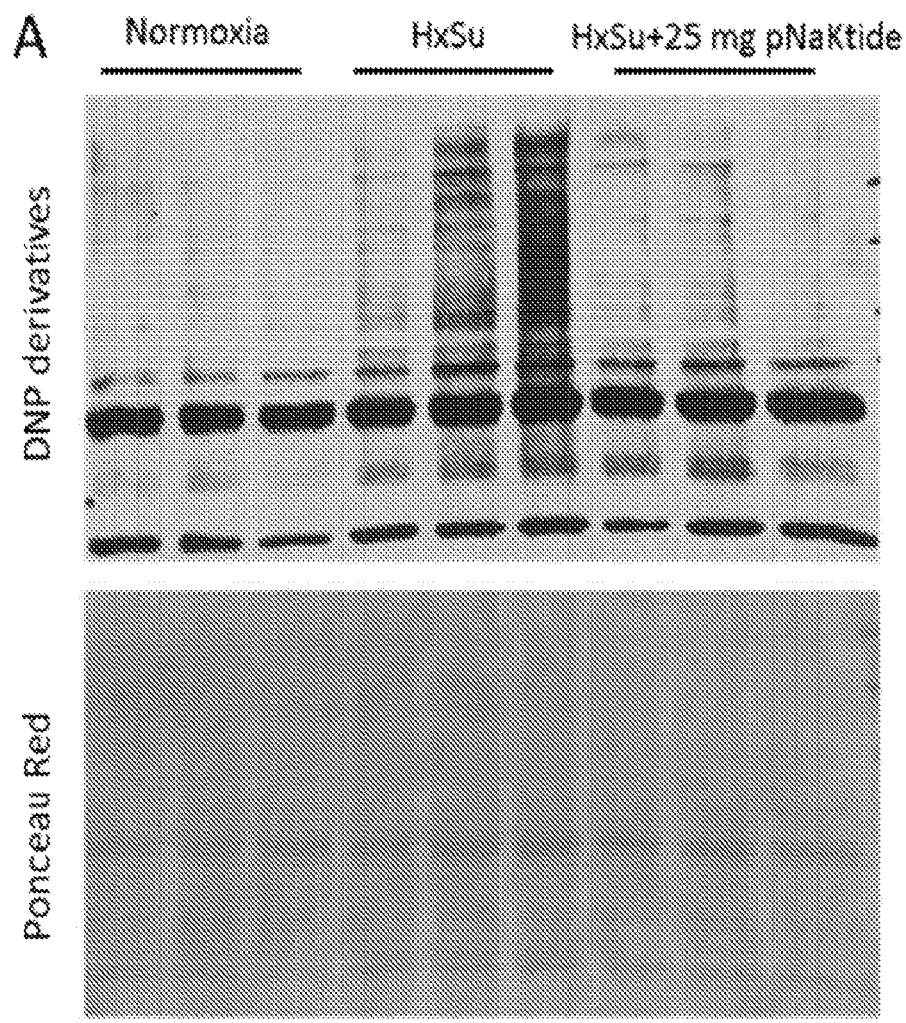
FIGS. 7A-7B include images and a graphs showing pNaKtide attenuated HxSu induced protein carbonylation in the lung, including.
Figure 7B:
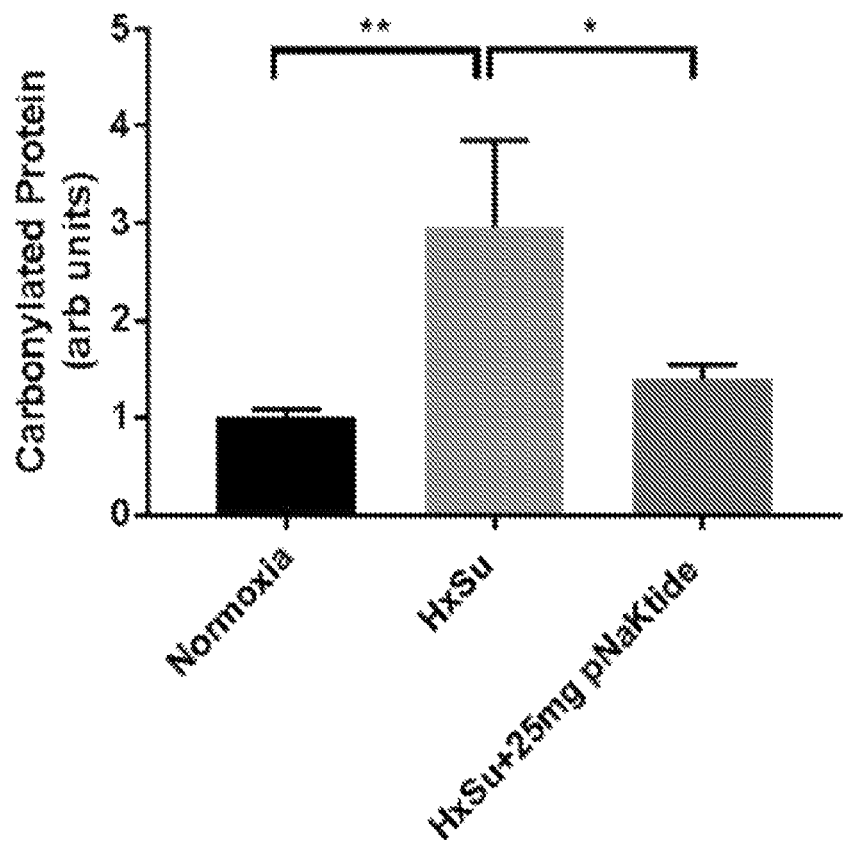

To assess the protein oxidation, protein carbonylation was tested in HxSu rats. HxSu significantly induced carbonylation of broad range of proteins compared with normoxic group (FIG. 7A). Treatment with pNaKtide (25 mg/kg/week) reduced the carbonylation to normal level (FIG. 7B).

Example 7—Mutation of Caveolin Binding Motif (CBM) of α1 NaKATPase Causes PAH and Right Ventricular Hypertrophy It has been observed that Na/K-ATPase-mediated signal transduction requires its interaction with caveolin-1. It has further been demonstrated that the conserved caveolin binding motif (CBM) at the N-terminus of the α1 subunit of Na/K-ATPase is required for its interaction with caveolin-1 and signaling, but not for exerting ion-pumping function. Moreover, a homozygous genotype (bearing a knocking in CBM mutant (F97A and F100A) on both alleles of the Na/K-ATPase al gene) results in embryonic lethality, whereas a heterozygous genotype (mCBM Het) shows no apparent phenotype. To address the potential off-target effect of pNaKtide and provide genetic evidence that al Na/K-ATPase is a key control mechanism for PAH, the pulmonary vasculature and the right heart of CBM Het mice was further studied.

Figure 8A:
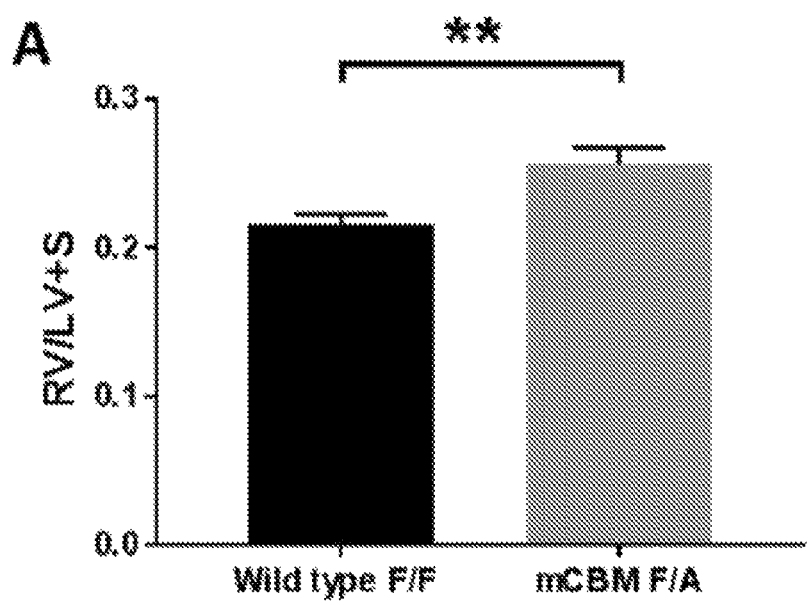
FIGS. 8A-8D include graphs showing RV hypertrophy and PH in cCBM heterozygous mice, including.
Figure 8B:
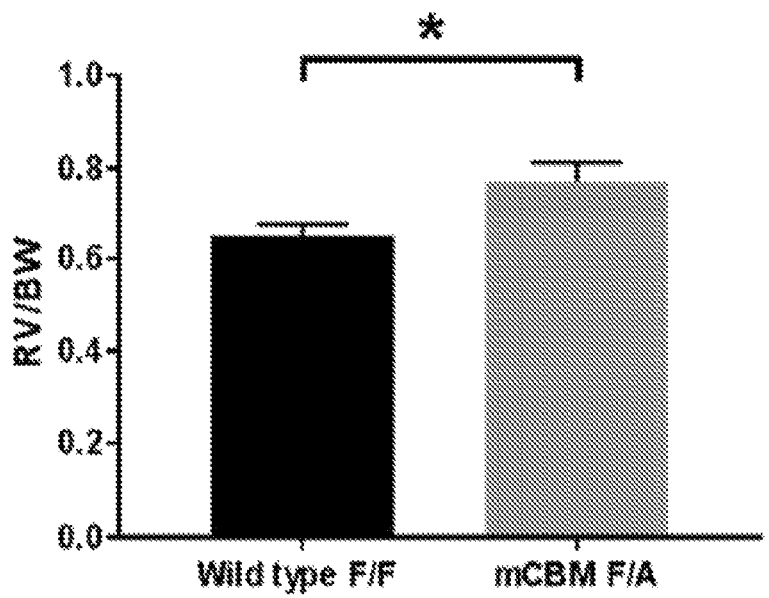
Figure 8C:
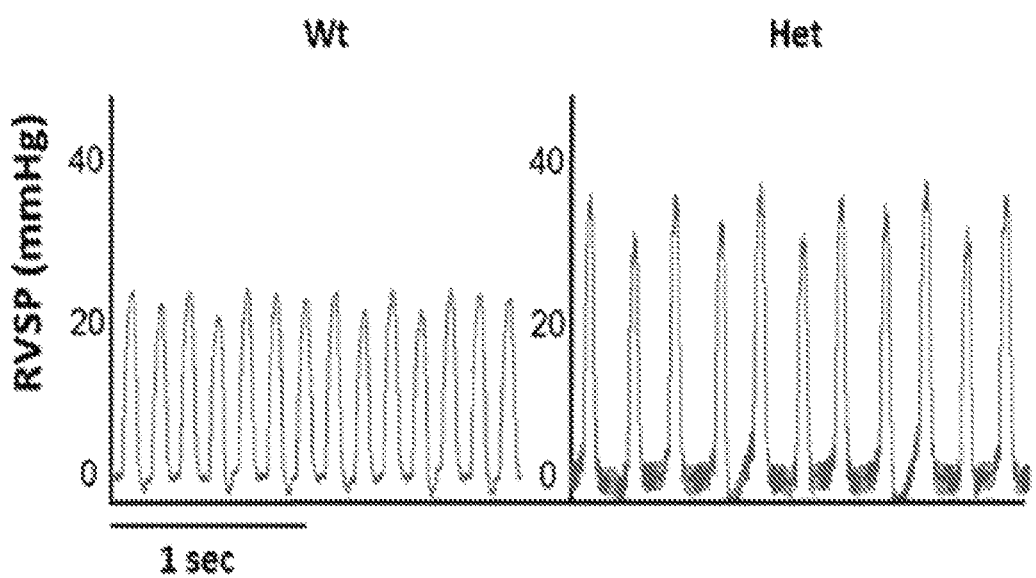
Figure 8D:
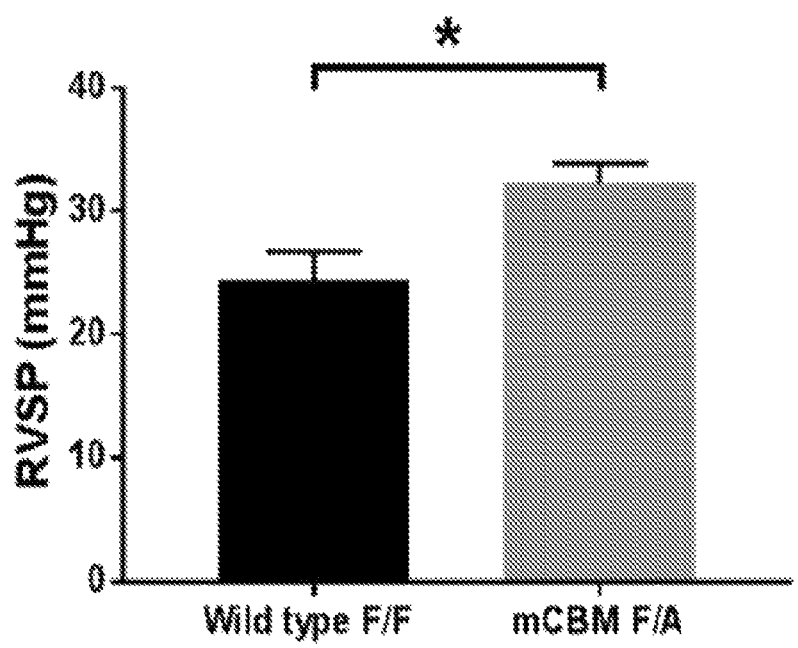

The Fulton index of mCBM heterozygous (Het) mice ($0.26\pm0.01$, n=6) was significantly increased compared with that of cCBM WT mice ($0.22\pm0.01$, n=8; $P<0.01$) (FIG. 8A). The RV/body weight ratio of mCBM heterozygous mice ($0.77\pm0.04$, n=6) was also elevated compared with that of mCBM WT mice ($0.65\pm0.03$, n=8; $P<0.05$) (FIG. 8B). Right ventricular systolic pressure (RVSP) was used to estimate the pulmonary artery systolic pressure. The RVSP of mCBM heterozygous mice had significantly increased RVSP compared with WT mice ($32.25\pm1.61$ mmHg versus $24.41\pm2.63$ mmHg) (FIGS. 8C-8D).

Example 9—mCBM Het Mice Develop Spontaneous Pulmonary Vascular Muscularization

The majority of lung small vessels are nonmuscularized (89.1%) in wt mice, the remainder showing partial (8.9%) or fully muscularization (2%). CBM het mice showed more partial (19.6%) and fully muscularized vessels (5.6%), reduced nonmuscularized vessels (78.1%) (FIGS. 9A-9B).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Liu, J., et al., Attenuation of Na/K-ATPase Mediated Oxidant Amplification with pNaKtide Ameliorates Experimental Uremic Cardiomyopathy. Sci Rep, 2016. 6: p. 34592.
2. Sodhi, K., et al., pNaKtide inhibits Na/K-ATPase reactive oxygen species amplification and attenuates adipogenesis. Sci Adv, 2015. 1(9): p. e1500781.
3. Badesch, D. B., et al., Diagnosis and assessment of pulmonary arterial hypertension. J Am Coll Cardiol, 2009. 54(1 Suppl): p. S55-66.
4. Hoeper, M. M. and R. G. J. Simon, The changing landscape of pulmonary arterial hypertension and implications for patient care. Eur Respir Rev, 2014. 23(134): p. 450-7.
5. McGoon, M. D., et al., Pulmonary arterial hypertension: epidemiology and registries. J Am Coll Cardiol, 2013. 62(25 Suppl): p. D51-9.
6. McLaughlin, V. V., et al., Management of pulmonary arterial hypertension. J Am Coll Cardiol, 2015. 65(18): p. 1976-97.
7. Schermuly, R. T., et al., Mechanisms of disease: pulmonary arterial hypertension. Nat Rev Cardiol, 2011. 8(8): p. 443-55.
8. Sitbon, O, et al., Long-term response to calcium channel blockers in idiopathic pulmonary arterial hypertension. Circulation, 2005. 111(23): p. 3105-11.
9. Packer, M., N. Medina, and M. Yushak, Adverse hemodynamic and clinical effects of calcium channel blockade in pulmonary hypertension secondary to obliterative pulmonary vascular disease. J Am Coll Cardiol, 1984. 4(5): p. 890-901.
10. Badlam, J. B. and T. M. Bull, Steps forward in the treatment of pulmonary arterial hypertension: latest developments and clinical opportunities. Ther Adv Chronic Dis, 2017. 8(2-3): p. 47-64.
11. Simonneau, G., et al., Updated clinical classification of pulmonary hypertension. J Am Coll Cardiol, 2013. 62(25 Suppl): p. D34-41.
12. Karlin, S. and S. F. Altschul, Methods for assessing the statistical significance of molecular sequence features by using general scoring schemes. Proc Natl Acad Sci USA, 1990. 87(6): p. 2264-8.
13. Karlin, S. and S. F. Altschul, Applications and statistics for multiple high-scoring segments in molecular sequences. Proc Natl Acad Sci USA, 1993. 90(12): p. 5873-7.
14. Altschul, S. F., et al., Basic local alignment search tool. J Mol Biol, 1990. 215(3): p. 403-10.
15. Taraseviciene-Stewart, L., et al., Inhibition of the VEGF receptor 2 combined with chronic hypoxia causes cell death-dependent pulmonary endothelial cell proliferation and severe pulmonary hypertension. Faseb j, 2001. 15(2): p. 427-38.
16. Yared, K., et al., Pulmonary artery acceleration time provides an accurate estimate of systolic pulmonary arterial pressure during transthoracic echocardiography. J Am Soc Echocardiogr, 2011. 24(6): p. 687-92.
17. Granstam, S. O., et al., Use of echocardiographic pulmonary acceleration time and estimated vascular resistance for the evaluation of possible pulmonary hypertension. Cardiovasc Ultrasound, 2013. 11: p. 7.
18. Ma, Z., L. Mao, and S. Raj agopal, Hemodynamic Characterization of Rodent Models of Pulmonary Arterial Hypertension. J Vis Exp, 2016(110).

19. Ciuclan, L., et al., A novel murine model of severe pulmonary arterial hypertension. Am J Respir Crit Care Med, 2011. 184(10): p. 1171-82.
20. Hoshikawa, Y., et al., Hypoxia induces different genes in the lungs of rats compared with mice. Physiol Genomics, 2003. 12(3): p. 209-19.
21. Alencar, A. K., et al., Beneficial effects of a novel agonist of the adenosine A2A receptor on monocrotaline-induced pulmonary hypertension in rats. Br J Pharmacol, 2013. 169(5): p. 953-62.
22. Abe, K., et al., Formation of plexiform lesions in experimental severe pulmonary arterial hypertension. Circulation, 2010. 121(25): p. 2747-54.
23. Bertero, T., et al., Vascular stiffness mechanoactivates YAP/TAZ-dependent glutaminolysis to drive pulmonary hypertension. J Clin Invest, 2016.
24. Yan, Y., et al., Involvement of reactive oxygen species in a feed-forward mechanism of Na/K-ATPase-mediated signaling transduction. J Biol Chem, 2013. 288(47): p. 34249-58.
25. Dostanic, I., et al., The alpha 1 isoform of Na,K-ATPase regulates cardiac contractility and functionally interacts and co-localizes with the Na/Ca exchanger in heart. J Biol Chem, 2004. 279(52): p. 54053-61.
26. Cai, T., et al., Regulation of caveolin-1 membrane trafficking by the Na/K-ATPase. J Cell Biol, 2008. 182(6): p. 1153-69.
27. Liu, J., et al., Ouabain-induced endocytosis of the plasmalemmal Na/K-ATPase in LLC-PK1 cells requires caveolin-1. Kidney Int, 2005. 67(5): p. 1844-54.
28. Wang, H., et al., Ouabain assembles signaling cascades through the caveolar Na+/K+-ATPase. J Biol Chem, 2004. 279(17): p. 17250-9.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating pulmonary arterial hypertension, comprising administering a polypeptide antagonist of a Na/K ATPase/Src receptor complex to a subject in need thereof, wherein the polypeptide antagonist comprises the sequence of SEQ ID NO: 1, or a functional fragment thereof.

2. The method of claim 1, wherein the polypeptide antagonist further includes a cell penetrating polypeptide having an amino acid sequence selected from the group consisting of SEQ ID NOS: 2-4.

3. The method of claim 1, wherein the polypeptide antagonist comprises the sequence of SEQ ID NO: 5, or a functional fragment thereof.

4. The method of claim 1, wherein the administering step includes oral administration, transdermal administration, administration by inhalation, nasal administration, topical administration, intraaural administration, rectal administration, intravenous administration, intramuscular administration, subcutaneous administration, intravitreous administration, subconjunctival administration, intracameral administration, intraocular administration or combinations thereof.

5. The method of claim 1, wherein administering the polypeptide antagonist comprises administering an amount of the polypeptide antagonist sufficient to reduce pulmonary artery acceleration time.

6. The method of claim 1, wherein administering the polypeptide antagonist comprises administering an amount of the polypeptide antagonist sufficient to reduce an amount of right ventricular hypertrophy.

7. The method of claim 6, wherein administering the polypeptide antagonist comprises administering an amount of the polypeptide antagonist sufficient to reduce right ventricular wall thickness.

8. The method of claim 1, wherein administering the polypeptide antagonist comprises administering an amount of the polypeptide antagonist sufficient to reduce an amount of pulmonary vessel wall thickness.

9. The method of claim 1, wherein administering the polypeptide antagonist comprises administering an amount of the polypeptide antagonist sufficient to reduce an amount of plexiform lesions in a lung of the subject.

10. The method of claim 1, wherein administering the polypeptide antagonist comprises administering an amount of the polypeptide antagonist sufficient to reduce an amount of collagen deposition in a pulmonary blood vessel of the subject.

11. The method of claim 10, wherein administering the polypeptide antagonist comprises administering an amount of the polypeptide antagonist sufficient to reduce an amount of collagen deposition in the pulmonary blood vessel media or adventitia.

12. The method of claim 1, wherein administering the polypeptide antagonist comprises administering an amount of the polypeptide antagonist sufficient to reduce an amount of right ventricular fibrosis.

13. The method of claim 1, wherein administering the polypeptide antagonist comprises administering an amount of the polypeptide antagonist sufficient to reduce an amount of IL-6 in the subject.

14. A method of reducing pulmonary vessel wall thickness, comprising administering a polypeptide antagonist of a Na/K ATPase/Src receptor complex to a subject in need thereof, wherein the polypeptide antagonist comprises the sequence of SEQ ID NO: 1, or a functional fragment thereof.

15. The method of claim 14, wherein the polypeptide antagonist comprises the sequence of SEQ ID NO: 5, or a functional fragment thereof.

16. The method of claim 14, wherein the subject has pulmonary arterial hypertension.

* * * * *